US008647337B2

(12) United States Patent
Niedbala et al.

(10) Patent No.: US 8,647,337 B2
(45) Date of Patent: Feb. 11, 2014

(54) DEVICES AND METHODS FOR DISPENSING A CRYOGENIC FLUID

(75) Inventors: R. Sam Niedbala, Allentown, PA (US); Lincoln C. Young, Ithaca, NY (US); Peng Zhou, Newtown, PA (US)

(73) Assignee: STC Consulting, LLC, Allentown, PA (US)

( * ) Notice: Subject to any disclaimer, the term of this patent is extended or adjusted under 35 U.S.C. 154(b) by 1152 days.

(21) Appl. No.: 12/489,875

(22) Filed: Jun. 23, 2009

(65) Prior Publication Data

US 2010/0319360 A1     Dec. 23, 2010

(51) Int. Cl.
    A61B 18/18    (2006.01)
    F17C 7/02     (2006.01)
    F17C 13/00    (2006.01)

(52) U.S. Cl.
    USPC ............... 606/26; 62/50.1; 62/50.7; 62/52.1; 606/20; 606/21; 606/22; 606/23; 606/25

(58) Field of Classification Search
    USPC ......... 62/50.1, 50.7, 52.1; 606/20, 22, 23, 25, 606/26, 21
    See application file for complete search history.

(56) References Cited

U.S. PATENT DOCUMENTS

| 3,439,680 A | 4/1969 | Thomas |
| 3,536,075 A | 10/1970 | Thomas |
| 3,933,075 A | 1/1976 | Lisenbee et al. |
| 4,201,319 A | 5/1980 | Andera et al. |
| 4,211,231 A * | 7/1980 | Rzasa ............................. 606/26 |
| 4,865,028 A | 9/1989 | Swart |
| 5,200,170 A | 4/1993 | McDow |
| 5,222,999 A * | 6/1993 | Bryne ............................... 374/5 |
| 5,330,745 A | 7/1994 | McDow |
| 5,516,505 A | 5/1996 | McDow |
| 5,738,682 A | 4/1998 | Jensma |
| 6,092,527 A | 7/2000 | Jensma |

(Continued)

FOREIGN PATENT DOCUMENTS

| EP | 0 608 954 B1 | 4/1997 |
| EP | 2292170 A2 | 3/2011 |

(Continued)

OTHER PUBLICATIONS

International Search Report for PCT International Application No. PCT/US2010/039423 dated Feb. 8, 2011.

(Continued)

*Primary Examiner* — John Pettitt
*Assistant Examiner* — Keith Raymond
(74) *Attorney, Agent, or Firm* — J.A. Lindeman & Co., PLLC

(57) ABSTRACT

A dispensing head for dispensing a cryogenic fluid may comprise a flow passage configured to be placed in flow communication with a reservoir containing a cryogenic fluid, the flow passage defining a flow passage inlet opening configured to receive the cryogenic fluid from the reservoir, and a flow passage outlet opening opposite the flow passage inlet opening. The dispensing head may further comprise a dispensing member configured to dispense the cryogenic fluid, the dispensing member defining a lumen having a lumen inlet opening and a lumen outlet opening; and at least one porous member disposed in the flow passage, the at least one porous member being configured as a primary flow regulation mechanism to limit a flow rate of the cryogenic fluid as it flows from the reservoir to the lumen outlet opening.

44 Claims, 11 Drawing Sheets

(56) References Cited

U.S. PATENT DOCUMENTS

| | | |
|---|---|---|
| 6,296,410 B1 | 10/2001 | Ruizendaal |
| 6,432,102 B2* | 8/2002 | Joye et al. .................. 606/21 |
| 6,602,247 B2* | 8/2003 | Lalonde .................. 606/22 |
| 7,364,689 B2 | 4/2008 | Noguchi et al. |
| 2002/0003322 A1 | 1/2002 | Dull et al. |
| 2004/0102768 A1 | 5/2004 | Cluzeau et al. |
| 2005/0043723 A1 | 2/2005 | Howlett et al. |
| 2005/0046063 A1 | 3/2005 | Toda et al. |
| 2005/0242455 A1 | 11/2005 | Toda et al. |
| 2005/0253311 A1 | 11/2005 | Nakamura et al. |
| 2006/0116670 A1 | 6/2006 | Scott et al. |
| 2006/0189968 A1 | 8/2006 | Howlett et al. |
| 2006/0213509 A1 | 9/2006 | Marin et al. |
| 2008/0208183 A1 | 8/2008 | Marin et al. |
| 2008/0221561 A1 | 9/2008 | Geiger et al. |
| 2009/0270851 A1 | 10/2009 | Babkin et al. |
| 2011/0152850 A1* | 6/2011 | Niedbala et al. ............. 606/25 |
| 2011/0152851 A1* | 6/2011 | Formica .................. 606/25 |

FOREIGN PATENT DOCUMENTS

| | | |
|---|---|---|
| GB | 1402632 A | 8/1975 |
| GB | 2336782 A | 3/1999 |
| WO | WO 96/17554 A1 | 6/1996 |
| WO | 2011/005495 A2 | 1/2011 |

OTHER PUBLICATIONS

Written Opinion of the International Searching Authority for PCT International Application No. PCT/US2010/039423 dated Feb. 8, 2011.

* cited by examiner

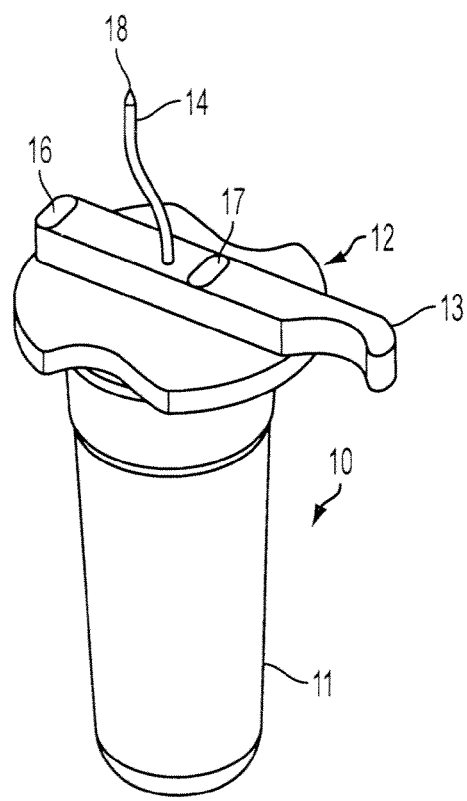
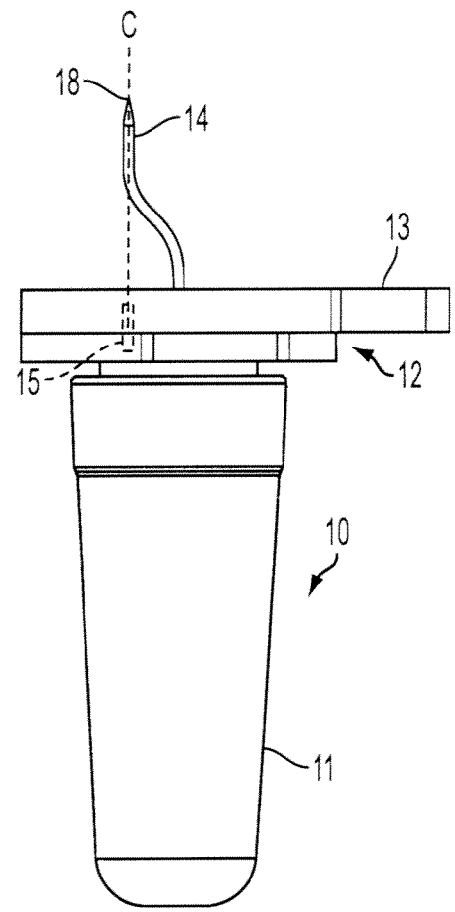
FIG. 1
FIG. 2

DEVICES AND METHODS FOR DISPENSING A CRYOGENIC FLUID

TECHNICAL FIELD

The present teachings relate to devices and methods for dispensing a cryogenic fluid. In particular, the present teachings relate to cryosurgical devices and methods for cooling surfaces by either directly dispensing a cryogenic fluid to a surface to be treated or by dispensing a cryogenic fluid onto an applicator to be placed in contact with a surface to be treated.

BACKGROUND

A number of procedures have been developed for treating superficial lesions, such as, for example, warts, on human and animal skin. Lesions can be removed, for example, through the localized freezing of the skin lesion tissue by a cooling fluid, such as a liquid refrigerant. Physicians have used liquid nitrogen applications, for example, to freeze and remove lesions from a patient's skin. Conventional methods of treatment, however, may have the disadvantages of requiring specialized equipment to condense the nitrogen gas, the need for specialized storage devices, and the inherent hazards of handling and dispensing materials having very low boiling points, for example, as low as approximately −196° C. in the case of liquid nitrogen.

More recently, various methods have been developed to treat skin lesions cryosurgically by employing a cooling fluid (e.g., a cryogenic fluid) contained, for example, in a handheld pressurized container. Such cryosurgical devices generally rely upon a liquefied (compressed) gas, such as, for example, butane, propane, or dimethyl ether (DME), to rapidly cool an applicator tip or "bud" based on the principles of "heat of vaporization." In other words, as the compressed gas flows to and contacts a surface of an applicator, such as, for example, a porous applicator bud, rapid evaporation of the gas causes the applicator surface to cool to temperatures which are lower than the temperature of the liquefied gas alone. In several such methods, an effective amount of the cryogenic fluid from the pressurized container can be dispensed, for example, into a hollow supply tube having a cotton, fiber and/or plastic foam bud located at the distal end of the supply tube. The cryogenic fluid accumulates in the applicator and upon evaporation, cools the applicator to temperatures well below freezing. The applicator can be placed in contact with the skin surface of the lesion for a period of time sufficient to reduce the temperature of the skin lesion tissue to temperatures that freeze the skin, such that permanent, irreversible rupture of the cellular membranes of the tissue occurs.

Cryosurgical devices currently utilizing the heat of vaporization principal in combination with compressed gases, such as DME for example, can pose various issues. For example, the devices can depend significantly upon the particular gas used and rates of evaporation from the applicator may be relatively long (e.g., on the order of 15-30 seconds). Moreover, the effective temperature of the applicator (i.e., the temperature of the applicator that is sufficient to cause freezing of the skin lesion) may be reached for only a short period of time, particularly once placed in contact with the warmer surface of the skin lesion, thereby limiting effective freezing of the target tissue.

Various additional cryosurgical devices can utilize liquid nitrogen, or other liquefied gases such as, for example, chlorofluoro carbons or nitrous oxide, which have significantly lower boiling points and thus can be dispensed at colder temperatures than some conventional "heat of vaporization" gases such as DME, thereby achieving more aggressive freezing effects. Such cryosurgical devices, however, are generally still relatively complex in their structure, using complicated valving mechanisms and dispensers to deliver the liquefied gas. Accordingly, problems can arise with such devices due to the high pressures exhibited by the gases the complicated manner in which the cryogenic fluid is moved from the container to the dispensing tip, the ease of use, and/or the cost associated with manufacture and/or assembly of the devices.

Accordingly, it may be desirable to provide a cryosurgical device that is both simple in terms of structure and use, and capable of delivering a variety of cryogenic fluids, including more aggressive cooling agents, such as, for example, nitrous oxide and liquid nitrogen, in an amount sufficient to achieve effective cryosurgical treatment. It may be further desirable to provide a disposable cryosurgical device that can be discarded once spent. It may, therefore, be desirable to provide an economical device with simpler structural components and flow regulation mechanisms, which can also reduce waste of the cryogenic fluid as it is moved from a container, for example to an applicator, for dispensing at a desired location.

SUMMARY

The present teachings may solve one or more of the above-mentioned problems and/or may demonstrate one or more of the above-mentioned desirable features. Other features and/or advantages may become apparent from the description that follows.

In accordance with various exemplary embodiments of the present teachings, a dispensing head for dispensing a cryogenic fluid may comprise a flow passage configured to be placed in flow communication with a reservoir containing a cryogenic fluid, the flow passage defining a flow passage inlet opening configured to receive the cryogenic fluid from the reservoir, and a flow passage outlet opening opposite the flow passage inlet opening. The dispensing head may further comprise a dispensing member configured to dispense the cryogenic fluid, the dispensing member defining a lumen having a lumen inlet opening and a lumen outlet opening; and at least one porous member disposed in the flow passage, the at least one porous member being configured as a primary flow regulation mechanism to limit a flow rate of the cryogenic fluid as it flows from the reservoir to the lumen outlet opening.

In accordance with various additional exemplary embodiments of the present teachings, a dispensing head for dispensing a cryogenic fluid may comprise a flow passage configured to be placed in flow communication with a reservoir containing a cryogenic fluid, the flow passage defining a flow passage inlet opening configured to receive the cryogenic fluid from the reservoir, and a flow passage outlet opening opposite the flow passage inlet opening. The dispensing head may further comprise a dispensing member configured to dispense the cryogenic fluid, the dispensing member defining a lumen having a lumen inlet opening and a lumen outlet opening; and an actuation member configured to move between a first position in which the flow passage outlet opening is not aligned and is blocked from flow communication with the lumen inlet opening, and a second position in which the flow passage outlet opening is aligned with and in flow communication with the lumen inlet opening.

In accordance with various further exemplary embodiments of the present teachings, a method for dispensing a cryogenic fluid may comprise coupling a dispensing head defining a flow passage, a dispensing member, an actuation member, and at least one porous member disposed in the flow passage to a container defining a reservoir. The method may further comprise actuating the dispensing head so as to move an inlet opening of the dispensing member from a first position in which an outlet of the flow passage is not aligned and is blocked from flow communication with the dispensing member inlet opening to a second position in which the flow passage outlet opening is aligned with and in flow communication with the dispensing member inlet opening. The method may further comprise flowing an amount of cryogenic fluid from the reservoir toward the dispensing member inlet opening through the flow passage and dispensing the cryogenic fluid from a dispensing member outlet opening to a target location wherein a flow rate of the cryogenic fluid flowing from the reservoir to the dispensing member outlet opening is primarily regulated by passing the cryogenic fluid through at least one porous member.

In accordance with various additional exemplary embodiments of the present teachings, a method for dispensing a cryogenic fluid may comprise placing an application member in contact with a skin surface and supplying a cryogenic fluid to the application member while the application member is in contact with the skin surface. The method may further comprise diffusing the cryogenic fluid through the application member to the skin surface at a temperature that is directly effective to freeze the skin surface such that permanent, irreversible rupture of cellular membranes of cells of the skin surface occurs while the cryogenic fluid is being delivered to the skin surface.

Additional objects and advantages will be set forth in part in the description which follows, and in part will be obvious from the description, or may be learned by practice of the present teachings. At least some of the objects and advantages may be realized and attained by means of the elements and combinations particularly pointed out in the appended claims.

It is to be understood that both the foregoing general description and the following detailed description are exemplary and explanatory only and are not restrictive of the claims; rather, the claims are entitled to their full breadth and scope, including equivalents.

BRIEF DESCRIPTION OF THE DRAWINGS

The present teachings can be understood from the following detailed description either alone or together with the accompanying drawings. The drawings are included to provide a further understanding, and are incorporated in and constitute a part of this specification. The drawings illustrate one or more exemplary embodiments of the present teachings and together with the description serve to explain various principles and operation.

FIG. 1 is a top perspective view of an exemplary embodiment of a device for dispensing a cryogenic fluid in accordance with the present teachings;

FIG. 2 is a side view of the device of FIG. 1;

DESCRIPTION OF EXEMPLARY EMBODIMENTS

Figure 3:
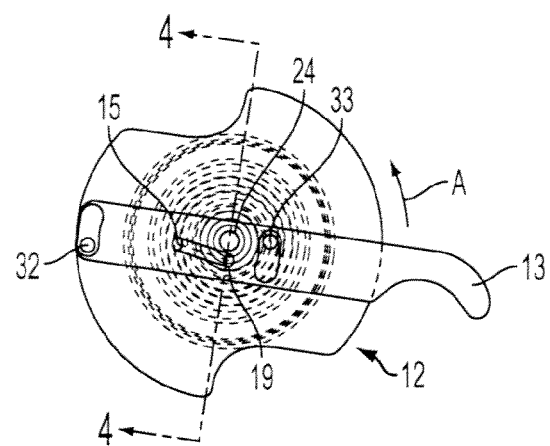
FIG. 3 is a top plan view of the device of FIG. 1, showing an actuation member in a first position.

The present teachings contemplate devices that are both relatively simple in structure and use, and capable of dispensing cryogenic fluid at sufficiently cold temperatures and pressures for a sufficient period of time so as to effect cryosurgical treatment. Devices and methods in accordance with the present teachings may dispense, for example, a sufficient and substantially uniform amount of a cryogenic fluid to an applicator to be placed in contact with a target freeze area, such as, for example, the tissue of a skin lesion. Devices in accordance with the present teachings may effectively treat and/or remove various types of skin lesions, including but not limited to, for example, verruca (warts), keratoses, achrocordon, molluscum contagiosum, age spots, dermatofibroma, keloids, granuloma, annulare, porokeratosis plantaris, angioman, lentigo discreta, chondrodermatitis, epithelial nevus, leokoplakia, granuloma pyogenicum, and/or kaposi's sarcoma.

To dispense the cryogenic fluid, dispensing heads in accordance with various exemplary embodiments of the present teachings may be used in conjunction with containers defining reservoirs containing a cryogenic fluid. The dispensing heads may provide, for example, an actuation member configured to move between a first position and a second position. When in a first position, the actuation member can block a flow passage outlet opening, thereby preventing the flow of the cryogenic fluid from the reservoir containing the cryogenic fluid and a dispensing member. When moved into a second position, however, the actuation member can align the flow passage outlet opening with a lumen inlet opening of the dispensing member, thereby placing the flow passage outlet opening in flow communication with the lumen inlet opening and allowing flow of the cryogenic fluid from the reservoir to the dispensing member.

To limit and/or regulate the flow rate of the cryogenic fluid, dispensing heads in accordance with various exemplary embodiments of the present teachings may utilize at least one porous member in the flow path of the cryogenic fluid. The at least one porous member may, for example, be configured as a primary flow regulation mechanism to limit the flow rate of the cryogenic fluid flowing from the reservoir through the porous member. As used herein, the term "primary flow regulation mechanism" refers to the main and/or sole mechanism for regulating the flow rate of the cryogenic fluid during dispensing of the cryogenic fluid from the reservoir and out of the device. As used herein, a "primary flow regulation mechanism" regulates the cryogenic fluid flow rate when the device is actuated (i.e., when the device is turned "on") so as to dispense the cryogenic fluid in an amount and at a rate sufficient to safely and effectively effectuate treatment (e.g., without which the flow rate would be too great to effectively use the device for its intended purpose). Thus, as used herein, "primary flow regulation" refers to regulating the cryogenic fluid flow rate once the device is turned on, as opposed to controlling activation of the device (i.e., turning the device "on" and "off" thereby respectively allowing and disallowing fluid flow from the reservoir to be dispensed to a treatment location). In other words, in at least some exemplary embodiments the flow path of the cryogenic fluid may be substantially free of other flow regulation mechanisms, such as, for example, needle valves, orifices, and/or finely cut dispensing tip diameters, other than the at least one porous member and thus flow regulation during actuation and dispensing occurs via the at least one porous member alone. In other exemplary embodiments, if additional flow regulation mechanisms are provided to regulate the flow rate of cryogenic fluid during dispensing of the fluid from a reservoir to a treatment location, such additional flow regulation mechanisms when used with a porous member as a "primary flow regulation mechanism" serve as a secondary regulation of the flow rate of the cryogenic fluid.

Figure 4:
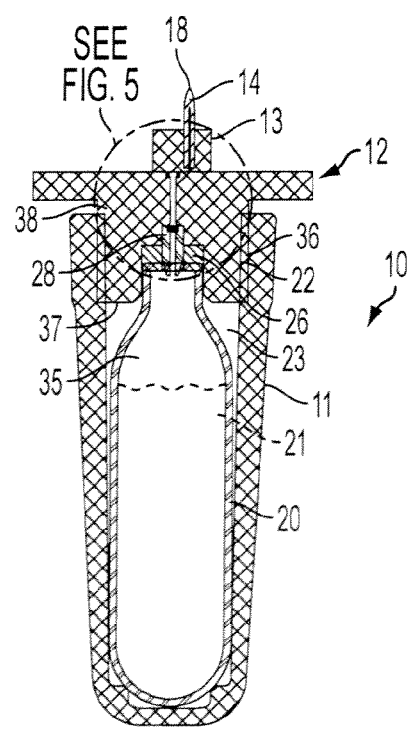
FIG. 4 is a cross-sectional view of the device of FIG. 1, taken along line 4-4 of FIG. 3.
Figure 5:
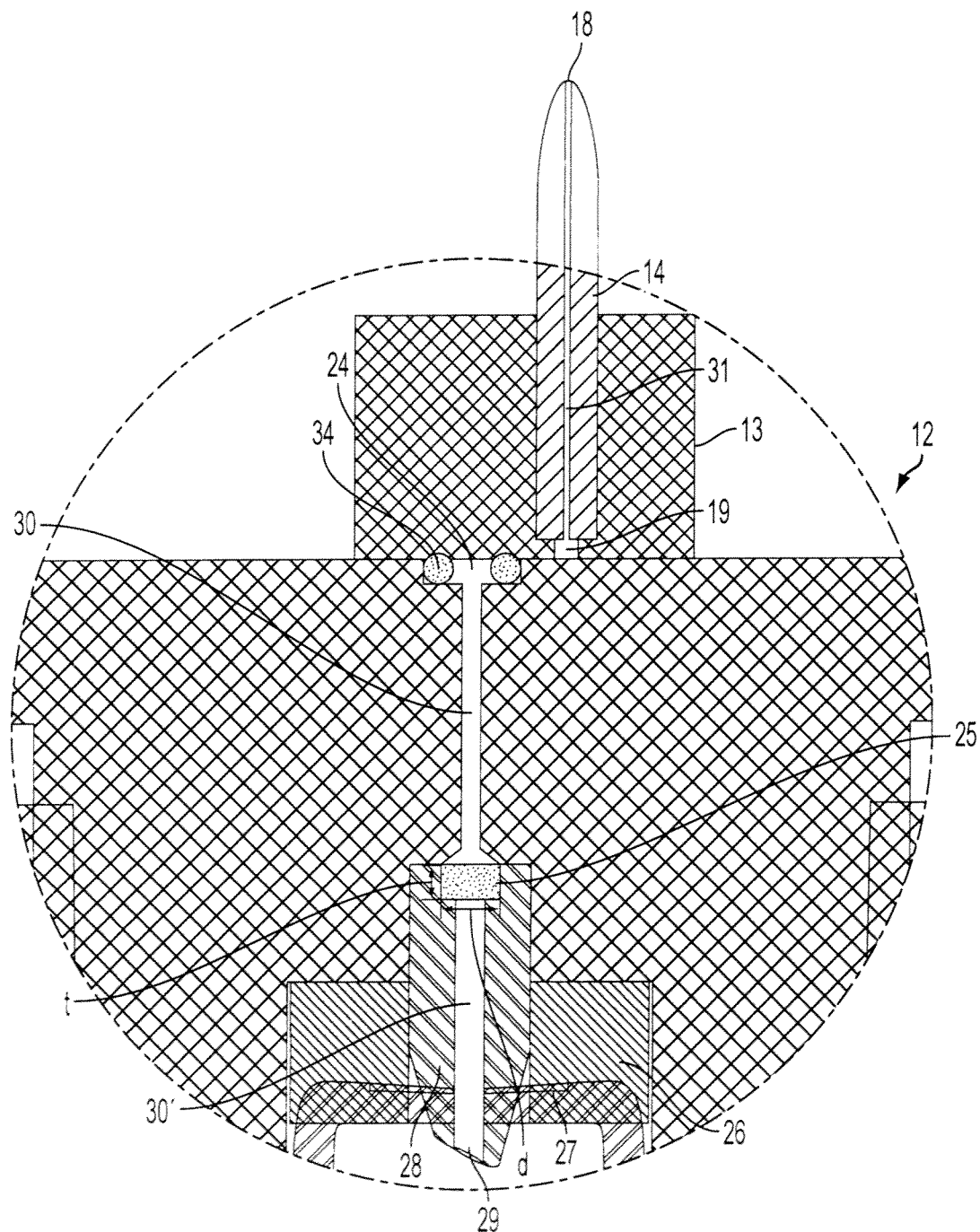
FIG. 5 is an enlarged view of the dispensing head of FIG. 4.
Figure 6:
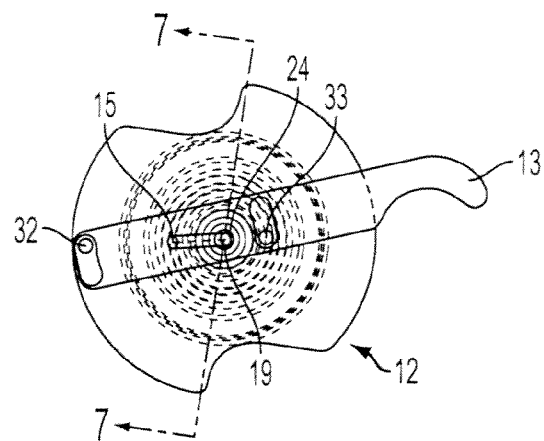
FIG. 6 is a top plan view of the device of FIG. 1, showing the actuation member in a second position.
Figure 7:
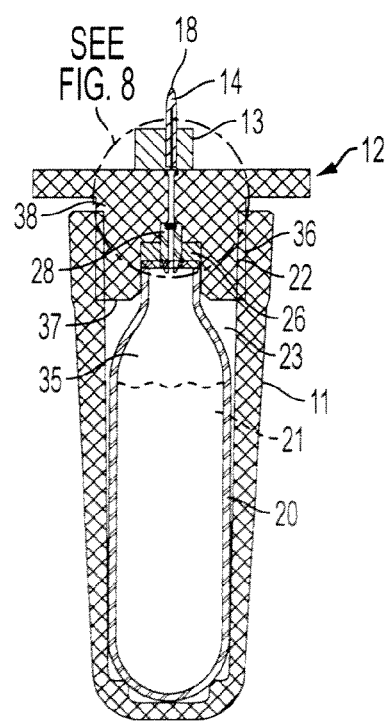
FIG. 7 is a cross-sectional view of the device of FIG. 1, taken along line 7-7 of FIG. 6.

FIGS. 1-8 illustrate an exemplary embodiment of a device for dispensing a cryogenic fluid in accordance with the present teachings. As illustrated in FIGS. 1 and 2, the device 10 for dispensing a cryogenic fluid includes a dispensing head 12, which can engage with a housing 11. As shown in FIGS. 4 and 7, the housing 11 defines a chamber 23 configured to receive a container 20 defining a reservoir 35 for containing a cryogenic fluid 21. The cryogenic fluid 21 may comprise any suitable cryogenic agent fluid and/or mixture of fluids capable of providing reduced temperatures suitable for producing permanent, irreversible rupture of the cellular membranes of a skin lesion tissue, such as, for example, halogenated hydrocarbons (e.g., tetrafluoromethane, trifluoromethane and 1,1,1,2-Tetrafluoroethane), dimethyl ether (DME), n-butane, isobutene, propane, chlorofloro carbons, nitrous oxide and/or liquid nitrogen.

Those skilled in the art would understand that due to the relatively high internal pressures of the container 20, the cryogenic fluid 21 may be in the form of a liquid or a gas/liquid mixture. Those skilled in the art would further understand that the cryogenic fluid 21 may comprise various mixtures of cryogenic substances, which can, for example, permit lower internal pressures of the container 20 to achieve a desired boiling point.

The container 20 is configured to maintain the cryogenic fluid 21 under pressure by a seal 27, as shown in FIG. 5, at least, for example, when the reservoir 35 is at conventional storage, transit, and operating temperatures. The container 20 may be formed from various materials, including, for example, plated steel, aluminum and/or a poly-lined material. The seal 27 may also be formed from various materials, including, for example, aluminum, steel, rubber, plastic and/or a synthetic material. Those ordinarily skilled in the art would understand that the type of material for the container 20 and the seal 27 can be chosen based on resistance to corrosion from contact with the cryogenic fluid 21, ability to withstand the internal pressures and temperatures associated with containing cryogenic fluids, such as, for example, liquid nitrogen, and other such factors.

In various exemplary embodiments of the present teachings the container 20 and other components of the device 10 may be disposable such that the entire device 10 can be thrown away when the cryogenic fluid 21 is used up. In various additional exemplary embodiments, the container 20 may be configured to be recharged with cryogenic fluid upon depletion. In various further exemplary embodiments, the container 20 may be replaced with a new container with cryogenic fluid upon depletion, and remaining components of the device 10 may be reusable.

As illustrated in FIGS. 4 and 7, the dispensing head 12 can be removably engageable with the housing 11 or at least movably engageable with the housing 11. Various exemplary embodiments of the present teachings contemplate, for example, providing the dispensing head 12 and housing 11 with mutually engageable screw threading so as to enable the dispensing head 12 to be moved (e.g. loosened from and tightened onto) the housing 11. In the exemplary embodiment of FIGS. 1-8, as best shown in FIGS. 4 and 7, screw threading 36 may be provided on an external surface of the dispensing head 12 and configured to engage with screw threading 22 on an inner surface of the housing 11. To first use the device 10, an operator may tighten the dispensing head 12 down into the housing 11 via screwing. The dispensing head 12 may define a recess 37 configured to receive at least a portion of a neck 38 of the container 20 when the dispensing head 12 is tightened down onto the housing 11. The dispensing head 12 may further include a hollow piercing member 28 at least partially disposed in the recess 37 and configured to puncture the seal 27, placing the reservoir 35 in flow communication with the dispensing head 12, as will be described in more detail below. Disposed in the recess 37 surrounding the hollow piercing member 28 is a sealing member 26 which may be a compression seal for example, configured to substantially prevent the cryogenic fluid 21 from leaking as it flows from the reservoir 35 through the hollow piercing member 28.

Various exemplary embodiments of the present teachings contemplate various additional piercing mechanisms to puncture seal 27. Those of ordinary skill in the art would understand, therefore, that the hollow piercing member 28 as shown and described herein is exemplary only and not intended to limit the scope of the present teachings. Also, although in the exemplary embodiment of FIGS. 1-8, screw threading is provided on an outer surface of the dispensing head 12 and an inner surface of the housing 11, those ordinarily skilled in the art would appreciate that the dispensing head could have an inner surface portion provided with screw threading configured to engage with screw threading provided on an outer surface of the housing 11.

Various exemplary embodiments of the present teachings (not shown) further contemplate that the dispensing head 12 can engage directly with container 20, which could eliminate the need for the housing 11. For example, to first use the device, an operator may engage screw threading provided on an inner portion of the dispensing head 12 onto screw threading provided on an outer portion of the container 20. As above, when the dispensing head 12 is tightened down onto the container 20, the hollow piercing member 28 can puncture the seal 27, placing the reservoir 35 in flow communication with the dispensing head 12.

Figure 8:
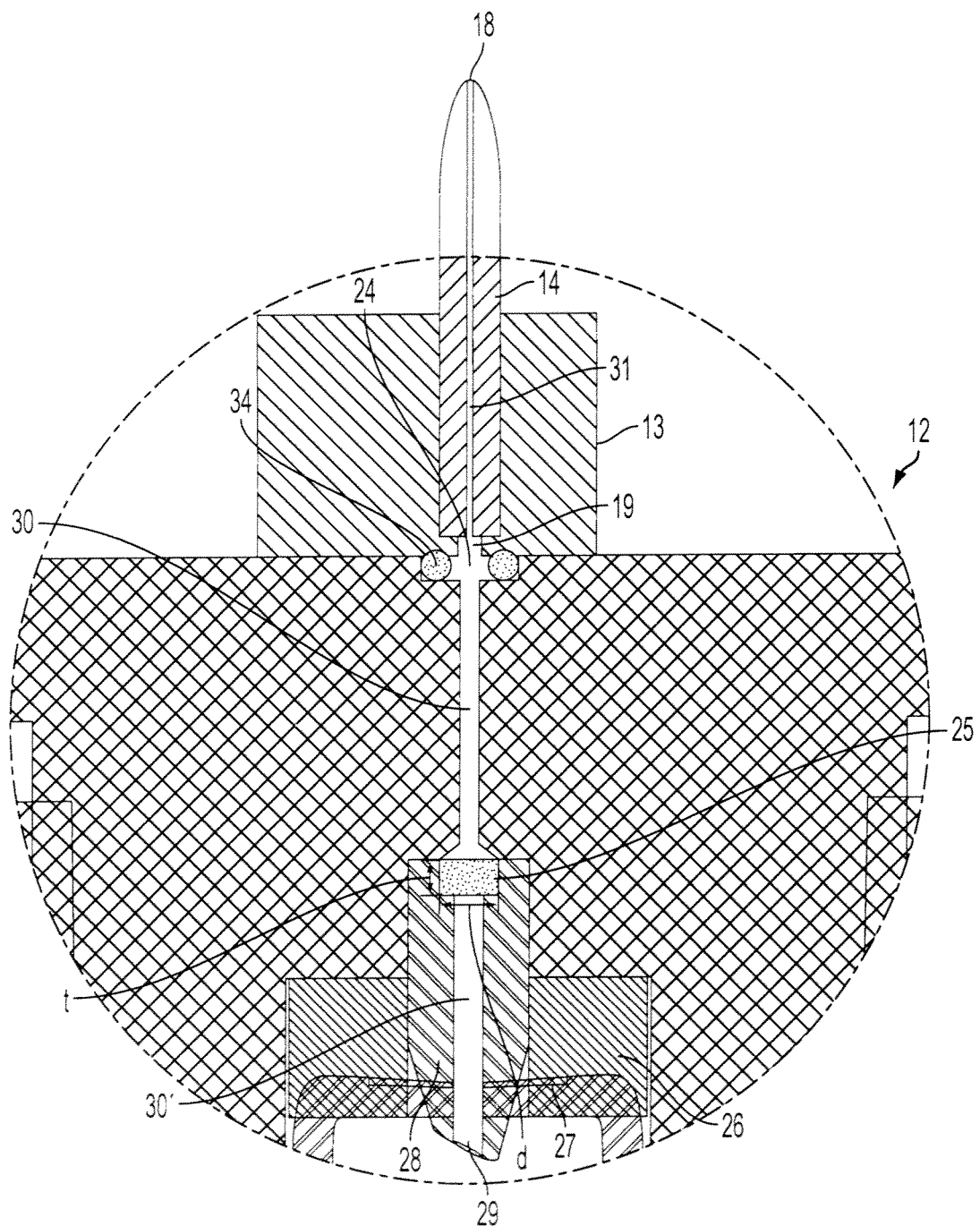
FIG. 8 is an enlarged view of the dispensing head of FIG. 7.

As illustrated in FIGS. 5 and 8, the dispensing head 12 includes a flow passage 30. The flow passage 30 defines, for example, a flow passage inlet opening 29 and a flow passage outlet opening 24. In various exemplary embodiments, for example, the flow passage 30 may include the hollow portion 30' of the hollow piercing member 28, which may define the flow passage inlet opening 29. Accordingly, when the dispensing head 12 is tightened down onto the housing 11, the hollow piercing member 28 can puncture the seal 27, placing the flow passage inlet opening 29 of the flow passage 30 in flow communication with the reservoir 35.

Those ordinarily skilled in the art would understand that the material, size and configuration of the flow passage 30 can be chosen based on the type of cryogenic fluid used, resistance to corrosion from contact with the cryogenic fluid, cost, efficiency and other such factors. To allow the cryogenic fluid 21 to travel in an effective and relatively short (i.e., direct) path between the flow passage inlet opening 29 and the flow passage outlet opening 24, various exemplary embodiments of the present teachings contemplate using a substantially straight flow passage 30.

Figure 9:
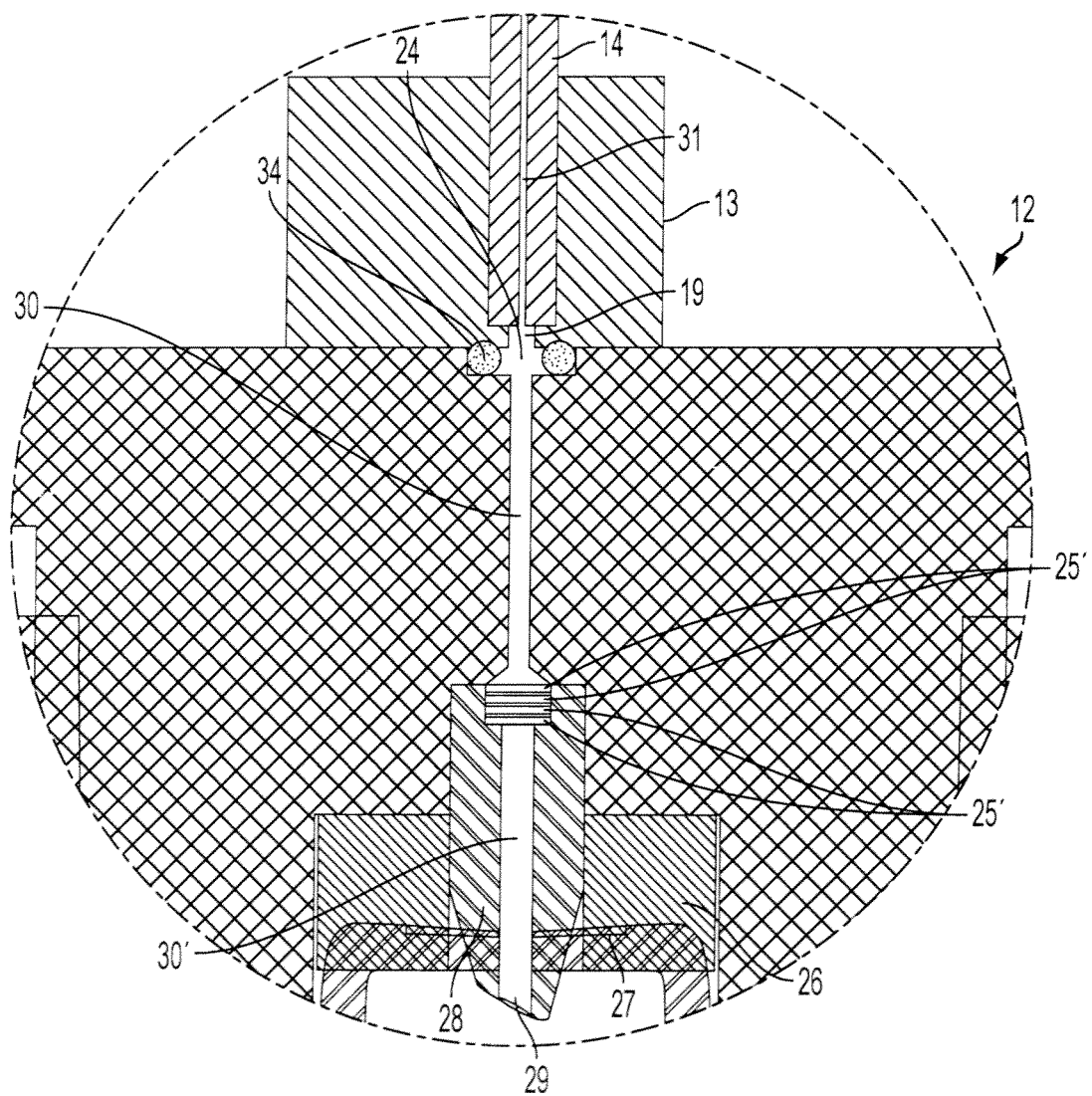
FIG. 9 is a partial enlarged view of another exemplary embodiment of a dispensing head in accordance with the present teachings.

As illustrated by FIGS. 5 and 8, the flow passage 30 includes at least one porous member 25. The at least one porous member 25 can be disposed in the flow passage 30 and configured as a primary flow regulation mechanism to limit a flow rate of the cryogenic fluid 21 that is dispensed from the dispensing head 12. Various exemplary embodiments of the present teachings consider, for example, a substantially disk-shaped porous member 25 having a thickness t ranging from about 0.5 mm to about 12.0 mm, a diameter d ranging from about 1.0 mm to about 5.0 mm, a porosity ranging from about 20% to about 35%, and a pore size ranging from about 0.1 μm to about 170 μm, for example, from about 1.0 μm to about 4.0 μm. Various additional exemplary embodiments of the present teachings consider a plurality (i.e., more than 1) of substantially disk-shaped porous members 25' stacked one on top of the other, as illustrated for example in FIG. 9. In various exemplary embodiments, each of the plurality of porous members 25' may have a thickness ranging from about 0.1 mm to about 3.0 mm and a diameter ranging from about 1.0 mm to about 5.0 mm. In the exemplary embodiment of FIG. 9, the plurality of porous members 25' may each have the same porosity, or at least one of the porous members 25' may have a porosity that differs from the other porous members 25'.

The at least one porous member 25 may be formed from any suitable material and/or combination of materials, including, for example, glass, plastic and/or metal. In various exemplary embodiments, the at least one porous member 25 may be a frit. Various exemplary embodiments in accordance with the present teachings, for example, contemplate that the at least one porous member 25 can be formed from a synthetic fluoropolymer, such as, for example, polytetrafluoroethylene (PTFE). Those ordinarily skilled in the art would understand that the type of material may be chosen based on efficiency, resistance to corrosion from contact with the cryogenic fluid 21, ability to withstand the internal pressures and temperatures that are generated and other factors. Various exemplary embodiments of the present teachings, for example, contemplate that the at least one porous member 25 may withstand a pressure of less than or equal to about 750 psi and a temperature ranging from about 0° C. to about −110° C.

Those ordinarily skilled in the art would further understand that the at least one porous member 25 can be cut and/or shaped as desired to properly fit and function within the flow passage 30, and need not be disk-shaped. For example, various exemplary embodiments of the present teachings contemplate that the at least one porous member 25 can be formed within the hollow portion 30' of the hollow piercing member 28.

Various exemplary embodiments of the present teachings consider that the at least one porous member 25 can both limit the flow rate of the cryogenic fluid 21 and filter contaminants out of the cryogenic fluid 21. The at least one porous member 25 may be configured to regulate the rate at which the cryogenic fluid 21 flows from the reservoir 35 to the outlet of the dispensing head 12 (e.g., to outlet 18 of a dispensing member 14) in order to achieve a desired flow rate of the cryogenic fluid 21 for dispensing to a desired location, whether that location is a lesion to be treated or an application member. In the case of cryosurgical applications, it may be desirable to meter the amount of cryogenic fluid that is dispensed during the time period in which the actuation member 13 is in the open position and the device is being used for cryosurgical freezing. Such regulation over the amount of fluid that flows from the dispensing member 18 can help to ensure that sufficient freezing takes place to effect the desired cryosurgical treatment, without over freezing and/or uncontrolled dispensing so as risk contacting locations other than the target location with the cryogenic fluid.

Various exemplary embodiments of the present teachings contemplate, for example, that the at least one porous member 25 is the only mechanism for regulating the flow rate of the cryogenic fluid 21 flowing from the reservoir 35 through the dispensing head 12 to the outlet of the lumen 31, for example, without valves or other similar active flow regulation mechanisms. Various additional exemplary embodiments of the present teachings further consider using various supplemental flow regulation techniques in combination with the at least one porous member 25. For example, in various exemplary embodiments the inner diameter of the flow passage 30 and/or of a lumen 31 in the dispensing member 14 can also help to regulate the flow rate and supplement the use of the at least one porous member 25 as the primary flow regulation mechanism.

As illustrated in FIGS. 1 and 2, the dispensing head 12 further includes an actuation member 13 and a dispensing member 14 carried by the actuation member 13. The actuation member 13 may be affixed to the base portion of the dispensing head 12 that connects to the container 11. Screws 32 and 33 (shown in FIGS. 3 and 6), which are located within screw holes 16 and 17 respectively, may be used to attach the actuation member 13; although such fixation is exemplary and non-limiting and those skilled in the art would understand other manners in which to fix the actuation member 13 to the base portion of the dispensing head 12. The actuation member 13 may move between a first position and a second position. For example, in the exemplary embodiment of FIGS. 1-8, the actuation member 13 may comprise a lever arm that can rotate the actuation member 13 about a center of rotation C between the first position and the second position. Movement of the actuation member 13 in turn can move the dispensing member 14, as will be explained in further detail below.

In various exemplary embodiments, the degree to which the actuation member 13 moves between the first and second positions can be controlled. For example, in the exemplary embodiment of FIGS. 1-8, the size (e.g., length) and configuration of the screw holes 16 and 17 can regulate how much the actuation member 13 can move between the first position and the second position. For example, in various embodiments, the configuration of the movement of the actuation member 13 may be chosen based on the degree of rotation desired for actuation member 13. As illustrated in FIGS. 3 and 6, various exemplary embodiments of the present teachings consider, for example, that screw holes 16 and 17 are sufficiently sized to allow actuation member 13 to rotate in a fixed path, with a fixed degree of rotation. Various exemplary embodiments contemplate, for example, that the actuation member 13 may rotate about 20 degrees between the first position and the second position. Those ordinarily skilled in the art would understand that the type, size and configuration of screws 32 and 33 can be chosen based on the size and configuration of screw holes 16 and 17, cost, efficiency and other such factors.

As illustrated in FIG. 2, in various exemplary embodiments of the present teachings, the actuation member 13 may rotate about a pin 15, which controls the center of rotation C of the actuation member 13 so that the center of rotation C substantially aligns with a lumen outlet opening 18 of the dispensing member 14. Accordingly, the actuation member 13 with the dispensing member 14 can rotate substantially without effecting the position of the lumen outlet opening 18 of the dispensing member 14.

In various exemplary embodiments the actuation member 13 may be biased, such as, for example, to move into a closed position when the actuation member 13 is not held in an open position. In other exemplary embodiments, the actuation member 13 may stay in the first or second position once moved there until a user moves the actuation member 13 back to the other position.

Figure 10:
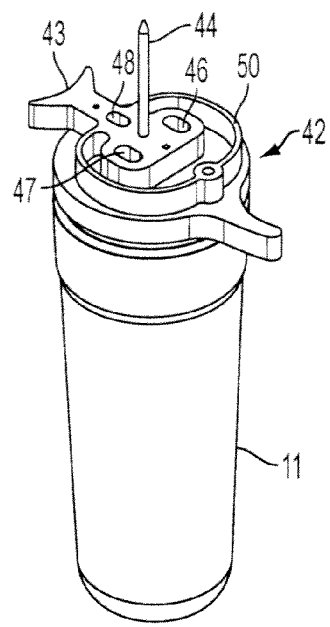
FIG. 10 is a top perspective view of another exemplary embodiment of a device for dispensing a cryogenic fluid in accordance with the present teachings.
Figure 11:
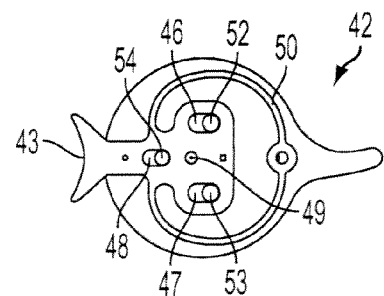
FIG. 11 is a top plan view of the device of FIG. 10.

As illustrated, for example, in FIGS. 10 and 11, various additional exemplary embodiments of the present teachings further consider a dispensing head 42 including an actuation member 43 comprising a lever arm that can slide the actuation member 43 between the first position and the second position. Movement of the actuation member 43 in turn can move a dispensing member 44, as will be explained in further detail below.

As before, in various exemplary embodiments, the degree of movement of the actuation member 43 between the first and second position may be controlled based on the configuration of the actuation member 43. For example, the size (e.g., length) and configuration of screw holes 46 and 47 and an alignment pinhole 48 can regulate how much the actuation member 43 moves between the first position and the second position. For example, in various embodiments, the size and configuration of the screw holes 46 and 47 and the alignment pinhole 48 can be chosen based on the degree of slide desired for actuation member 43. As illustrated in FIG. 11, various exemplary embodiments of the present teachings consider, for example, that the screw holes 46 and 47 and the alignment pinhole 48 are sufficiently sized to allow actuation member 43 to slide in a fixed path, with a fixed degree of movement between the first position and the second position.

Those ordinarily skilled in the art would understand that the type, size and configuration of screws 52 and 53 and an alignment pin 54 can be chosen based on the size and configuration of the screw holes 46 and 47 and the alignment pinhole 48, cost, efficiency and other such factors. In various exemplary embodiments, for example, the alignment pinhole 48 and the alignment pin 54 may be replaced, for example, with an additional screw hole and screw.

In various exemplary embodiments of the present teachings, the actuation member 43 may be biased, such as, for example, to move into a closed position when the actuation member 43 is not held in an open position. As illustrated in FIG. 11, for example, the actuation member 43 may comprise a tension spring 50 to slide into a closed position when the actuation member 43 is not held in an open position. In other exemplary embodiments the actuation member 43 may stay in either the first position or the second position once moved there until a user moves the actuation member 43 back to the other position.

Remaining components of the cryosurgical device of the exemplary embodiment of FIGS. 10 and 11 are the same as those described with reference to the exemplary embodiments of FIGS. 1-8 and are therefore not described in detail herein.

With reference again to FIGS. 3-5, the device 10 is shown with the actuation member 13 of the dispensing head 12 in a first position, wherein flow of the cryogenic fluid 21 out of the flow passage 30 and into the dispensing member 14 is blocked.

As illustrated in FIGS. 4 and 5, the actuation member 13 is positioned so that the flow passage outlet opening 24 is not aligned with and is blocked from flow communication with a lumen inlet opening 19 of the dispensing member 14, thereby preventing flow of the cryogenic fluid 21 from the container 20 to the dispensing member 14. In other words, in this position of the actuation member 14, the device 10 is "off," and can be actuated or tuned "on," for example, by moving the actuation member 13 (e.g., along path A in FIG. 3 or in the exemplary embodiment of FIGS. 10 and 11 moving actuation member 43 toward a center of the device) to a second position.

With reference now to FIGS. 6-8, the device 10 is shown with the actuation member 13 of the dispensing head 12 in a position wherein flow of the cryogenic fluid 21 out of the dispensing member 14 is allowed.

As illustrated in FIGS. 7 and 8, the actuation member 13 is positioned so that the flow passage outlet opening 24 is aligned with and in flow communication with the lumen inlet opening 19, thereby allowing flow of the cryogenic fluid 21 from the container 20 to the dispensing member 14.

The dispensing member 14 defines a lumen 31 having a lumen inlet opening 19 and a lumen outlet opening 18. As described above, and illustrated in FIG. 8, when the actuation member 13 is in the position shown, the lumen inlet opening 19 can be aligned with the flow passage outlet opening 24, creating a flow path between the flow passage inlet opening 29 and the lumen outlet opening 18 to dispense the cryogenic fluid 21. To allow the cryogenic fluid 21 to travel along a path configured to minimize losses and dispensing time, various exemplary embodiments of the present teachings consider that, in the second position, the actuation member 13 can form a substantially straight flow path for the cryogenic fluid 21 between the flow passage inlet opening 29 and the lumen inlet opening 19.

As shown best in FIGS. 5 and 8, the dispensing head 12 may include a sealing member 34, such as, for example, a high durometer o-ring valve, surrounding the flow passage outlet opening 24 and disposed adjacent the actuation member 13. The sealing member 34 may prevent leakage of fluid 21 between the flow passage outlet opening 24 and the actuation member 13. To prevent failure of the sealing member 34 at high pressures, for example, various exemplary embodiments of the present teachings consider a 90 A durometer oaring. Those ordinarily skilled in the art would understand, however, that various types of sealing mechanisms may be used without departing from the scope of the present teachings.

The dispensing member 14 may be made of any suitable material and/or combination of materials, including, for example, glass, plastic and/or metal. Various exemplary embodiments in accordance with the present teachings contemplate, for example, that the dispensing member 14 can be made of the organic polymer polyaryletheretherketone (PEEK). Those skilled in the art would understand, therefore, that a variety of materials may be chosen for the dispensing member 14 based on cost, efficiency, resistance to corrosion from contact with the cryogenic fluid 21, ability to withstand the temperatures that are generated and other factors.

The dispensing member 14 can dispense the cryogenic fluid 21 via the lumen outlet opening 18. Various exemplary embodiments of the present teachings, for example, contemplate that the dispensing member 14 can dispense the cryogenic fluid 21 at a temperature ranging from about −20° C. to about −100° C. at the lumen outlet opening 18. In various exemplary embodiments, the dispensing member 14 can dispense the cryogenic fluid 21, for example, directly onto a target freeze area, such as, for example, a skin lesion. In various additional exemplary embodiments, the dispensing member 14 can dispense the cryogenic fluid 21 onto an outer surface portion of an applicator that is separate from the device 10 for subsequent application to the skin lesion via the applicator. Yet further exemplary embodiments contemplate that the dispensing member 14 can dispense the cryogenic fluid 21 to an applicator, for example, into a central portion of an applicator, attached in flow communication with the lumen outlet opening 18. Accordingly, the dispensing member 14, including the lumen outlet opening 18, can have various sizes, shapes and/or configurations based upon a desired application and/or treatment. Those ordinarily skilled in the art would understand, therefore, that the dispensing member 14, as depicted in FIGS. 1-8, is exemplary only, and a variety of dispensing mechanisms may be utilized to dispense cryogenic fluid out of the container 20.

Figure 12:
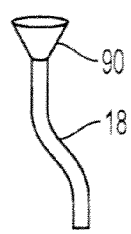
FIG. 12 is a perspective view of an exemplary embodiment of a dispensing member in accordance with the present teachings.

For direct dispensing applications, for example, an inner diameter of the lumen outlet opening 18 can control the spray and/or jet pattern of the cryogenic fluid 21. For this purpose, various exemplary embodiments of the present teaching consider the lumen outlet opening 18 having an inner diameter ranging from about 0.003 inches to about 0.030 inches. Various exemplary embodiments of the present teachings further consider a variety of hollow fluid retaining and/or constricting devices, such as, for example, a contact cone or receiver, which can be used in conjunction with the device 10, to pool the cryogenic fluid and limit the spread of the freeze to a directed location. Disposable fluid retaining devices 90, such as, for example, neoprene cones or commonly available otoscopic cones, can attach directly to the lumen outlet opening 18, as depicted in FIG. 12, and be removed after each use or treatment.

Figure 13:
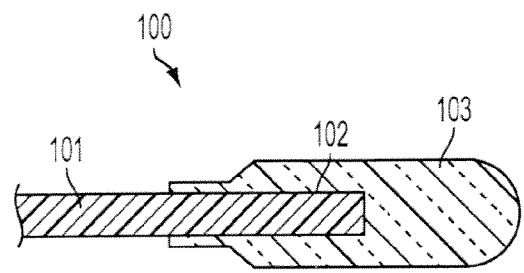
FIG. 13 is a cross-sectional view of an exemplary embodiment of an applicator in accordance with the present teachings.

As mentioned above, the dispensing member 14 can also dispense (e.g., spray and/or drip) the cryogenic fluid 21 onto an applicator separate from the device 10 for subsequent application to a skin lesion via the applicator. FIG. 13 illustrates an exemplary applicator 100 that can be used in conjunction with the device 10. The applicator 100 may include, for example, a gripping portion, such as a stem 101, and an application member, such as for example a bud-shaped tip 103, disposed on and secured to an end 102 of the stem 101. The dispensing member 14 can dispense the cryogenic fluid 21 directly onto an outer surface of the bud-shaped tip 103, where the cryogenic fluid 21 may accumulate on the bud-shaped tip 103 and may evaporate therefrom to cool the bud-shaped tip 103. The bud-shaped tip 103 can then be placed in contact with the skin surface of the lesion to cryosurgically treat the lesion.

Figure 14:
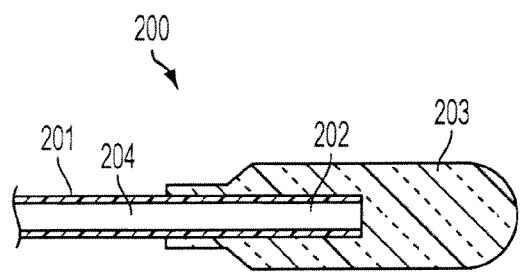
FIG. 14 is a cross-sectional view of another exemplary embodiment of an applicator in accordance with the present teachings.

In an alternative exemplary embodiment, the dispensing member 14 can dispense the cryogenic fluid 21 to an applicator in flow communication with the lumen outlet opening 18. FIG. 14 illustrates an exemplary embodiment of an applicator 200 that can be attached to the device 10. The applicator 200 may include, for example, a hollow tube 201, defining a passage 204, in flow communication with the lumen outlet opening 18 of the dispensing member 14. The hollow tube 201 includes an open discharge end 202, which may be surrounded by an application member, such as for example a bud-shaped tip 203. Alternatively, the bud-shaped tip 203 may be inserted directly over the dispensing member 14, without the intervening tube 201. When the device 10 is actuated, for example, the cryogenic fluid 21 can flow from the lumen outlet opening 18 into the passage 204 of the hollow tube 201, where the cryogenic fluid 21 may accumulate inside the bud-shaped tip 203 and evaporate, thereby cooling the bud-shaped tip 203 via heat of vaporization principles. The bud-shaped tip 203 can then be placed in contact with the skin surface of the lesion to cryosurgically treat the lesion in accordance with the present teachings. In various exemplary embodiments, for example, the bud-shaped tip 203 and tube 201 may be removed from the dispensing member 14 once filled and then the bud-shaped tip 203 may be placed in contact with the target freeze area.

Figure 15:
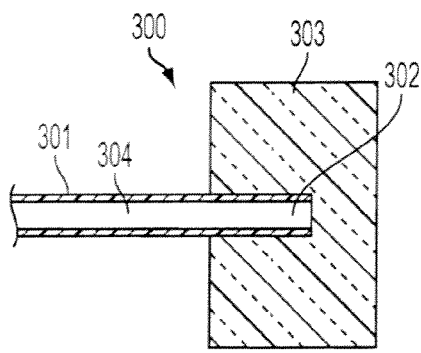
FIG. 15 is a cross-sectional view of another exemplary embodiment of an applicator in accordance with the present teachings.

FIG. 15 illustrates an additional exemplary embodiment of an applicator 300 that can be attached to the device 10. The applicator 300 may include, for example, a hollow tube 301, defining a passage 304, in flow communication with the lumen outlet opening 18 of the dispensing member 14. The hollow tube 301 includes an open discharge end 302, which may be surrounded by an application member, such as for example a disk-shaped tip 303. Alternatively, the disk-shaped tip 303 may be inserted directly over the dispensing member 14, without the intervening tube 301. In various exemplary embodiments of the present teachings, the disk-shaped tip 303 can be placed in contact with a skin surface of a lesion. When the device 10 is actuated, for example, the cryogenic fluid 21 can flow from the lumen outlet opening 18 into the passage 304 of the hollow tube 301 (or directly into a central portion of the disk-shaped tip 303), where the cryogenic fluid 21 may accumulate inside the disk-shaped tip 303 and diffuse to the skin surface of the lesion at a temperature that is directly effective to freeze the skin surface such that permanent, irreversible rupture of cellular membranes of cells of the skin surface occurs while the cryogenic fluid is being delivered to the skin surface.

Application members in accordance with various exemplary embodiments of the present teachings, such as, for example, bud-shaped tips 103 and 203 and disk-shaped tip 303, can be made of any suitable porous and/or absorbent material, such as, for example, Porex®, cotton wool, open-celled foams, a sintered thermoplastic, a sintered metal, a glass or ceramic frit, or a polyolefin or polyester non-woven fabric. Those ordinarily skilled in the art would further understand that the above disclosed bud-shaped tips 103 and 203 and disk-shaped tip 303 are exemplary only and that application members in accordance with the present teachings can have various shapes and sizes without departing from the scope of the present teachings. Those ordinarily skilled in the art would understand, for example, that the material, size, shape and/or configuration of the applicator used can be chosen based upon the desired treatment and/or temperature requirements. For example, in various exemplary embodiments, the dispensing member 14 can dispense the cryogenic fluid 21 to an application member configured to cool through heat of vaporization.

In accordance with various exemplary embodiments of the present teachings, an exemplary method for using the device 10 of the exemplary embodiment of FIGS. 1-8 will now be described. To dispense a sufficient and substantially uniform amount of a cryogenic fluid 21 to cryosurgically treat a lesion, such as for example, a skin lesion, an operator may, for example, couple the dispensing head 12 to the housing 11 holding the sealed container 20 filled with a cryogenic fluid 21. The dispensing head 12, for example, may be tightened down onto the housing 11 via engagement of screw threading 22 with screw threading 36. As the dispensing head 12 is tightened down relative to the housing 11, the hollow piercing member 28 may breach the seal 27 on the container 20, placing the flow passage 30 of the dispensing head 12 in flow communication with the reservoir 35 containing the cryogenic fluid 21.

The operator may then invert the device 10 such that the cryogenic liquid in the reservoir 35 is closer to the flow passage inlet opening 29 than is a gas in the reservoir 35. The operator may actuate the dispensing head 12, for example, by rotating the actuation member 13 in the direction of arrow A in FIG. 3 from a first position (shown in FIGS. 3-5), in which an outlet 24 of the flow passage 30 is not aligned and is blocked from flow communication with a dispensing member inlet opening 19, to a second position (shown in FIGS. 6-8), in which the flow passage outlet opening 24 is aligned with and in flow communication with the dispensing member inlet opening 19. Upon actuation, an amount of cryogenic fluid 21 may flow from the reservoir 35 toward the dispensing member inlet opening 19 through the flow passage 30, wherein the flow rate of the cryogenic fluid is primarily regulated by passing the cryogenic fluid 21 through at least one porous member 25 in the flow passage 30. The operator may then dispense the cryogenic fluid from the dispensing member 14 to a target location.

In various additional exemplary embodiments, the operator may actuate the dispensing head 42, for example, by sliding the actuation member 43 toward a center of the device from a first position, in which an outlet 24 of the flow passage 30 is not aligned and is blocked from flow communication with a dispensing member inlet opening 49, to a second position, in which the flow passage outlet opening 24 is aligned with and in flow communication with the dispensing member inlet opening 49. Upon actuation, an amount of cryogenic fluid 21 may flow from the reservoir 35 toward the dispensing member inlet opening 49 through the flow passage 30, wherein the flow rate of the cryogenic fluid is primarily regulated by passing the cryogenic fluid 21 through at least one porous member 25 in the flow passage 30. The operator may then dispense the cryogenic fluid from the dispensing member 44 to a target location.

Various exemplary embodiments of the present teachings contemplate, for example, dispensing the cryogenic fluid 21 directly onto a surface to be treated from the dispensing outlet 18, or flowing or dispensing the cryogenic fluid to an applicator first for subsequent application to the surface to be treated.

For example, in accordance with various exemplary embodiments of the present teachings, an exemplary method for dispensing a cryogenic fluid via an applicator of the exemplary embodiment of FIG. 15 will now be described. To dispense a sufficient and substantially uniform amount of a cryogenic fluid 21 to cryosurgically treat a lesion, such as for example, a skin lesion an operator may place an application member, such as, for example disk-shaped tip 303, in contact with a skin surface, and supply the cryogenic fluid 21 to the application member while the application member is in contact with the skin surface. The application member may be adapted to diffuse the cryogenic fluid to the skin surface at a temperature that is directly effective to freeze the skin surface such that permanent, irreversible rupture of cellular membranes of cells of the skin surface occurs while the cryogenic fluid is being delivered to the skin surface. For example, the application member may comprise a Porex® material or other similar sintered thermoplastic or metal, that may diffuse the cryogenic fluid to the skin surface. In an exemplary embodiment wherein the cryogenic fluid is liquid nitrogen or nitrous oxide, the cryogenic fluid may be delivered to the skin's surface at a temperature ranging from about −90° C. to about −110° C.

EXAMPLES

As discussed above, the present teachings contemplate devices that are capable of dispensing a regulated flow of a cryogenic fluid sufficiently cold enough for effective cryosurgical treatment, without over-freezing and/or undesired contact of the cryogenic fluid with other surfaces, such as, for example, healthy tissue or skin surrounding a lesion. To verify the flow regulation capabilities of devices and methods in accordance with exemplary embodiments of the present teachings, various laboratory tests were conducted with and without a porous member disposed in the flow passage. A dispensing head in accordance with the present teachings (i.e., with at least one porous member disposed in the flow passage), for example, demonstrated a flow rate of about 0.035 grams/second, whereas a dispensing head with an unobstructed flow passage (i.e., without a porous member disposed in the flow passage) demonstrated a flow rate of about 0.248 grams/second. Accordingly, given an 8 gram container of cryogenic fluid, a device which utilized the dispensing head without at least one porous member depleted its supply of cryogenic fluid much faster than a device which utilized the dispensing head with at least one porous member (e.g., 32 seconds vs. 228 seconds). Assuming a treatment time of 3 seconds per application, the device which utilized the dispensing head without at least one porous member could, therefore, only perform approximately 10 treatments, whereas the device which utilized the dispensing head with at least one porous member could perform approximately 76 treatments. The tests, therefore, demonstrated that the devices and methods in accordance with exemplary embodiments of the present teachings can dispense a regulated flow of a cryogenic fluid in order to achieve a desired treatment regime.

Figure 16:
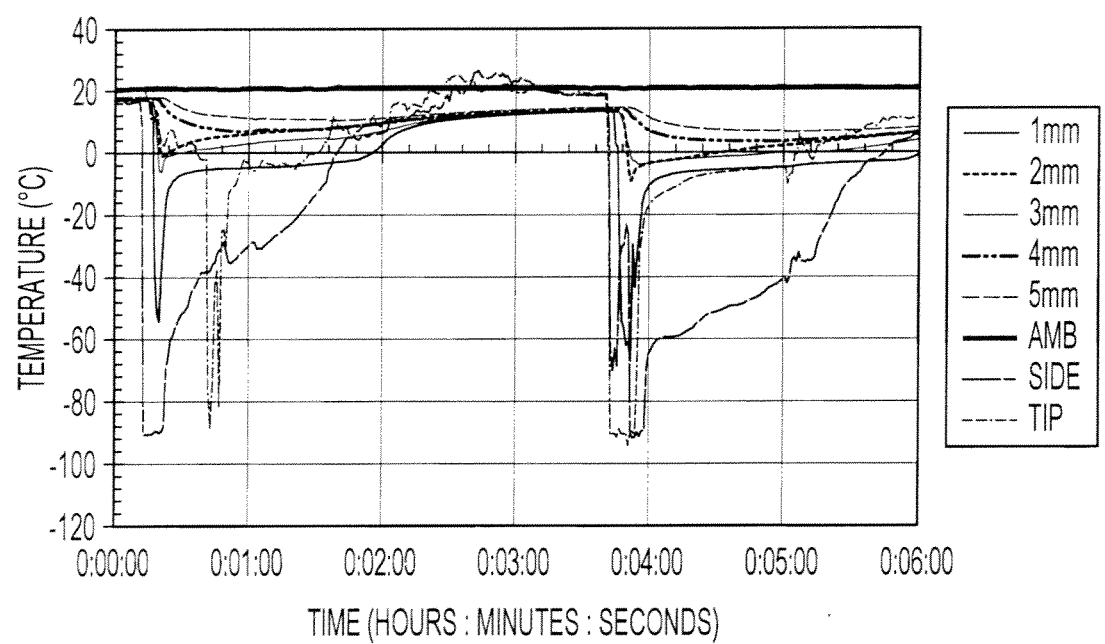
FIG. 16 is a graph of temperature versus time obtained from experiments using a device in accordance with the present teachings.
Figure 17:
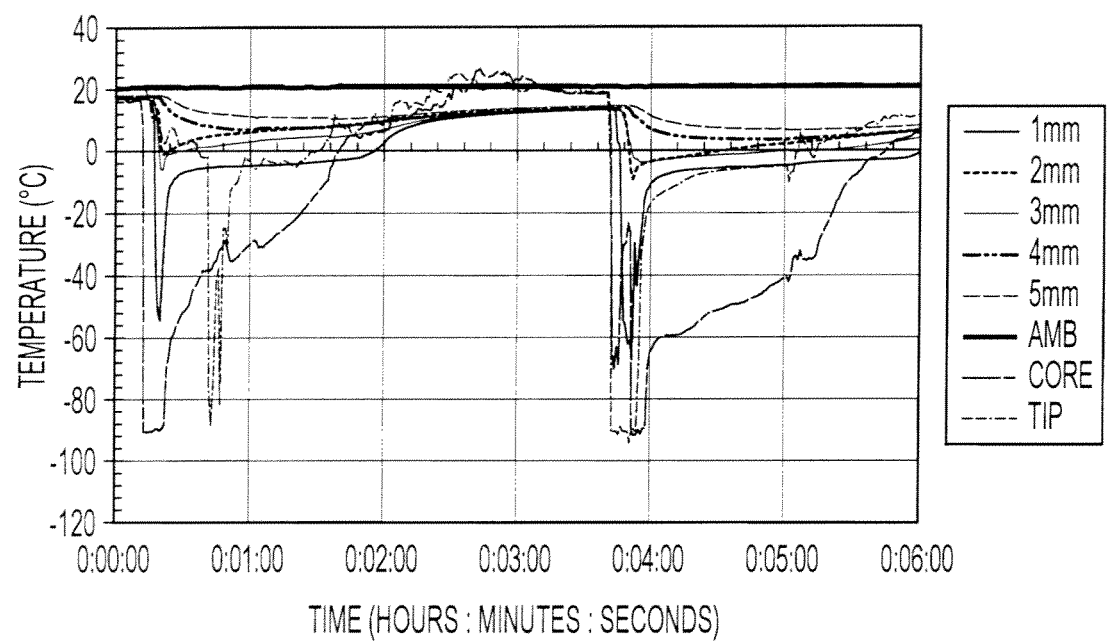
FIG. 17 is a graph of temperature versus time obtained from experiments using another device in accordance with the present teachings.
Figure 18:
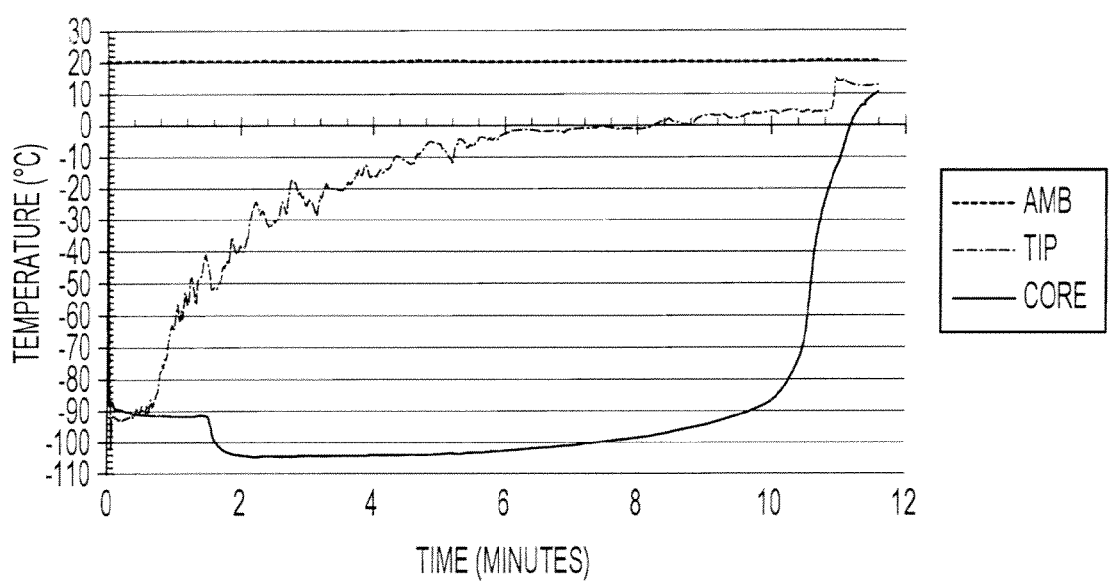
FIG. 18 is a graph of temperature versus time obtained from experiments using yet another device in accordance with the present teachings.

To further verify the cooling efficiency of devices and methods in accordance with exemplary embodiments of the present teachings, various additional laboratory tests were conducted with the results being illustrated in FIGS. 16-18.

In FIG. 16, for example, a device having a configuration similar to that of FIGS. 1-8 in accordance with the present teachings was used to dispense nitrous oxide ($N_2O$) directly onto a target freeze area on a gelatin material which was used to simulate skin lesion tissue. In the experiment, two open sprays of $N_2O$ were applied directly to the gelatin surface and thermocouples were used to measure the ambient temperature (i.e., AMB in FIG. 16), temperatures at the lumen outlet opening 18 (i.e., TIP in FIG. 16) and the area adjacent to the lumen outlet opening (i.e., SIDE in FIG. 16), and at different depths in the gelatin (i.e., 1 mm, 2 mm, 3 mm, 4 mm and 5 mm in FIG. 16). FIG. 16 is a plot of the measured temperatures over a six minute period.

As illustrated by the TIP thermocouple data in FIG. 16, the device was able to dispense $N_2O$ at temperatures as low as about −90°. This resulted in an almost immediate freezing of the target area to about −56° C., as demonstrated by the 1 mm thermocouple reading.

In FIG. 17, a device having a configuration similar to that of the exemplary embodiment of FIGS. 1-8 in accordance with the present teachings was used in conjunction with a porous polyethylene (50 μm pores) application member to apply nitrous oxide (N₂O) onto the target freeze area of a gelatin material used to simulate skin lesion tissue. In the experiment, N₂O was dispensed into the application member (i.e., in flow communication with the lumen outlet opening of the device similar to the applicator shown in FIG. 15) in two, ten second intervals while the application member was in contact with the gelatin surface and thermocouples were used to measure ambient temperature (i.e., AMB in FIG. 17), temperatures at the disk-shaped tip (i.e., TIP in FIG. 17) and the applicator core (i.e., CORE in FIG. 17), and at different depths in the gelatin (i.e., 1 mm, 2 mm, 3 mm, 4 mm and 5 mm in FIG. 17). FIG. 17 is a plot of the measured temperatures over a six minute period.

As illustrated by the TIP thermocouple trace in FIG. 17, the device was again able to dispense N₂O via the applicator at temperatures as low as about −90° C. This resulted in an almost immediate freezing of the target area to about −56° C., as demonstrated by the 1 mm thermocouple reading.

In FIG. 18, a device having a configuration similar to that of the exemplary embodiment of FIGS. 1-8 in accordance with the present teachings was used in conjunction with an open-celled foam application member to demonstrate heat of vaporization cooling. In the experiment, N₂O was dispensed into the application member (i.e., in flow communication with the lumen outlet opening of the device similar to the applicator shown in FIG. 14) and the application member was allowed to cool for approximately 30 seconds (i.e., to allow for heat of vaporization cooling) prior to contact with the gelatin surface. Thermocouples were used to measure ambient temperature (i.e., AMB in FIG. 18), and temperatures at the bud-shaped tip (i.e., TIP in FIG. 18) and the applicator core (i.e., CORE in FIG. 18). FIG. 18 is a plot of the measured temperatures over a twelve minute period.

As illustrated by the TIP thermocouple trace in FIG. 18, the application member exhibited an almost immediate drop in temperature to about −100° C. as the N₂O evaporated from the applicator (i.e., through heat of vaporization).

Accordingly, FIGS. 16-18 demonstrate that the devices and methods in accordance with exemplary embodiments of the present teachings can dispense cryogenic fluids so as to achieve cooling of application members as low as about −100° C.

For the purposes of this specification and appended claims, unless otherwise indicated, all numbers expressing quantities, percentages or proportions, and other numerical values used in the specification and claims, are to be understood as being modified in all instances by the term "about" if they are not already. Accordingly, unless indicated to the contrary, the numerical parameters set forth in the following specification and attached claims are approximations that may vary depending upon the desired properties sought to be obtained by the present teachings. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the present teachings are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

It should be understood that while the invention has been described in detail with respect to various exemplary embodiments thereof, it should not be considered limited to such, as numerous modifications are possible without departing from the broad scope of the appended claims.

We claim:

1. A dispensing head for dispensing a cryogenic fluid, comprising:
   a flow passage configured to be placed in flow communication with a reservoir containing the cryogenic fluid, the flow passage defining a flow passage inlet opening configured to receive the cryogenic fluid from the reservoir, and a flow passage outlet opening opposite the flow passage inlet opening;
   a dispensing member, separate from the flow passage, and configured to dispense the cryogenic fluid, the dispensing member defining a lumen having a lumen inlet opening and a lumen outlet opening;
   at least one porous member disposed in the flow passage between the flow passage inlet opening and the flow passage outlet opening and through which the cryogenic fluid flows, the at least one porous member configured as a primary flow regulation mechanism to limit a flow rate and pressure of the cryogenic fluid as the cryogenic fluid flows from the reservoir to the lumen outlet opening; and
   a movable actuation member, including the dispensing member, and configured to move laterally across a sealing member between a first position in which the flow passage outlet opening is not aligned and is blocked from flow communication with the lumen inlet opening, and a second position in which the flow passage outlet opening is aligned along a common central axis with the lumen inlet opening and is in flow communication with the lumen inlet opening to dispense the cryogenic fluid onto a skin surface via the lumen outlet opening.

2. The dispensing head of claim 1 further comprising:
   a sealing member disposed proximate the flow passage outlet opening and adjacent to the actuation member and configured to substantially prevent the cryogenic fluid from leaking as the cryogenic fluid flows from the flow passage outlet opening to the lumen inlet opening of the dispensing member in the actuation member.

3. The dispensing head of claim 1, wherein in the second position of the actuation member, a flow path from the flow passage inlet opening to the lumen inlet opening is substantially linear.

4. The dispensing head of claim 1, wherein the actuation member is configured to rotate or slide between the first position and the second position.

5. The dispensing head of claim 4, wherein a center of movement of the actuation member substantially aligns with the lumen outlet opening of the dispensing member.

6. The dispensing head of claim 1, wherein the dispensing member is configured to dispense the cryogenic fluid at a temperature ranging from 20° C. to −110° C.

7. The dispensing head of claim 1, wherein the dispensing member is configured to spray the cryogenic fluid.

8. The dispensing head of claim 1, further comprising:
   an applicator in flow communication with the lumen outlet opening of the dispensing member.

9. The dispensing head of claim 8, wherein the applicator comprises an open-celled foam structure in flow communication with the lumen outlet opening.

10. The dispensing head of claim 8, wherein the applicator comprises a porous glass, plastic, metal or natural fiber material.

11. The dispensing head of claim 1, wherein the at least one porous member comprises at least one porous material configured to withstand a pressure up to about 750 psi at room temperature and a temperature ranging from 0° C. to −110° C.

12. The dispensing head of claim 11, wherein the at least one porous material comprises glass, plastic and/or metal.

13. The dispensing head of claim 1, wherein the at least one porous member has a thickness ranging from 0.5 mm to 12.0 mm.

14. The dispensing head of claim 1, wherein the at least one porous member has a porosity ranging from 20% to 35%.

15. The dispensing head of claim 1, wherein the at least one porous member has a pore size ranging from 0.1 µm to 4 µm.

16. The dispensing head of claim 1, wherein the at least one porous member comprises a plurality of porous members.

17. The dispensing head of claim 16, wherein the plurality of porous members have a thickness ranging from 0.1 mm to 60 mm.

18. The dispensing head of claim 1, wherein the at least one porous member is substantially disk-shaped and has a diameter ranging from 1.0 mm to 5.0 mm.

19. The dispensing head of claim 1, wherein the flow rate of the cryogenic fluid dispensed from the dispensing member is about 0.035 g/sec.

20. The dispensing head of claim 1, further comprising a hollow piercing member in flow communication with the flow passage.

21. A device for dispensing a cryogenic fluid, comprising:
a container defining a reservoir containing the cryogenic fluid; and
the dispensing head of claim 1, wherein the reservoir in flow communication with the flow passage is the reservoir defined by the container.

22. The device of claim 21, wherein the dispensing head is configured to engage with the container.

23. The device of claim 21, wherein the device is configured so that when in use for dispensing, a cryogenic liquid in the reservoir is closer to the flow passage inlet opening than a gas in the reservoir.

24. The device of claim 21, wherein the dispensing head further comprises a hollow piercing member configured to breach a portion defining the container to place the flow passage in flow communication with the reservoir.

25. The device of claim 24, wherein the hollow piercing member is configured to breach the portion of the container upon engaging the dispensing head with a housing in which the container is disposed.

26. The device of claim 21, wherein the container is disposable.

27. A dispensing head for dispensing a cryogenic fluid, comprising:
a flow passage configured to be placed in flow communication with a reservoir containing the cryogenic fluid, the flow passage defining a flow passage inlet opening configured to receive the cryogenic fluid from the reservoir, and a flow passage outlet opening opposite the flow passage inlet opening;
a dispensing member, separate from the flow passage, and configured to dispense the cryogenic fluid, the dispensing member defining a lumen having a lumen inlet opening and a lumen outlet opening; and
a movable actuation member, including the dispensing member, and configured to move between a first position in which the flow passage outlet opening is not aligned and is blocked from flow communication with the lumen inlet opening, and a second position in which the flow passage outlet opening is aligned along a common central axis with the lumen inlet opening and is in flow communication with the lumen inlet opening to dispense the cryogenic fluid onto a skin surface via the lumen outlet opening.

28. The dispensing head of claim 27, furthering comprising at least one porous member disposed in the flow passage, the at least one porous member being configured as a primary flow regulation mechanism to limit a flow rate of the cryogenic fluid as the cryogenic fluid flows from the reservoir to the lumen outlet opening.

29. The dispensing head of claim 27, wherein in the second position of the actuation member, a flow path from the flow passage inlet opening to the lumen inlet opening is substantially linear.

30. The dispensing head of claim 27, wherein the actuation member is configured to rotate or slide between the first position and the second position.

31. The dispensing head of claim 30, wherein a center of rotation of the actuation member substantially aligns with the lumen outlet opening.

32. A method for dispensing a cryogenic fluid, comprising:
coupling a dispensing head defining a flow passage, a dispensing member, an actuation member, and at least one porous member disposed in the flow passage between a flow passage inlet opening and a flow passage outlet opening to a container defining a reservoir;
actuating the actuation member of the dispensing head so as to move a lumen inlet opening of the dispensing member from a first position in which a flow passage outlet opening is not aligned and is blocked from flow communication with the lumen inlet opening of the dispensing member across a sealing member, to a second position in which the flow passage outlet opening is aligned along a common central axis with the lumen inlet opening and is in flow communication with the lumen inlet opening of the dispensing member;
flowing an amount of cryogenic fluid from the reservoir toward the lumen inlet opening of the dispensing member through the flow passage; and
dispensing the cryogenic fluid from a lumen outlet opening in the dispensing member to a skin surface,
wherein a flow rate of the cryogenic fluid flowing from the reservoir to the dispensing member outlet opening is primarily regulated by passing the cryogenic fluid through the at least one porous member.

33. The method of claim 32, wherein coupling the dispensing head to the container comprises engaging screw threading on the dispensing head with screw threading on the container.

34. The method of claim 32, wherein coupling the dispensing head to the container comprises breaching a seal on the container.

35. The method of claim 32, wherein actuating the dispensing head comprises moving an actuation member from a first position to a second position.

36. The method of claim 32, wherein dispensing the cryogenic fluid comprises dispensing the cryogenic fluid directly onto the skin surface.

37. The method of claim 36, wherein dispensing the cryogenic cooling fluid directly onto the skin surface comprises flowing the cryogenic fluid through a contact cone or receiver.

38. The method of claim 32, wherein dispensing the cryogenic fluid comprises flowing the cryogenic fluid to an applicator.

39. The method of claim 32, further comprising coupling the dispensing member to an applicator.

40. The method of claim 39, further comprising placing the applicator to which the cryogenic fluid has flowed in contact with the skin surface.

41. The method for dispensing a cryogenic fluid of claim 32 further comprising:
- placing an application member in contact with the skin surface;
- supplying the cryogenic fluid to the application member while the application member is in contact with the skin surface; and
- diffusing the cryogenic fluid through the application member to the skin surface at a temperature that is directly effective to freeze the skin surface such that permanent, irreversible rupture of cellular membranes of cells of the skin surface occurs while the cryogenic fluid is being delivered to the skin surface.

42. The method of claim 41, wherein placing an application member in contact with the skin surface comprises placing a porous polyethylene application member in contact with the skin surface.

43. The method of claim 41, wherein supplying a cryogenic fluid to the application member while the application member is in contact with the skin surface comprises filling a hollow tube with the cryogenic fluid, wherein the hollow tube includes an open discharge end surrounded by the application member.

44. The method of claim 41, wherein the application member is adapted to diffuse the cryogenic fluid to the skin surface at a temperature ranging from 90° C. to −110° C.

* * * * *